(12) United States Patent
Kime et al.

(10) Patent No.: US 11,030,885 B2
(45) Date of Patent: Jun. 8, 2021

(54) SYSTEM AND METHOD FOR PROCESSING MULTIPLE SIGNALS

(71) Applicant: CHRONOLIFE, Paris (FR)

(72) Inventors: Sihem Kime, Courbevoie (FR); Guillaume Chenegros, Bassou (FR); Claire Marin, Paris (FR)

(73) Assignee: CHRONOLIFE, Paris (FR)

( * ) Notice: Subject to any disclaimer, the term of this patent is extended or adjusted under 35 U.S.C. 154(b) by 0 days.

(21) Appl. No.: 16/980,283

(22) PCT Filed: Mar. 13, 2019

(86) PCT No.: PCT/EP2019/056340
§ 371 (c)(1),
(2) Date: Sep. 11, 2020

(87) PCT Pub. No.: WO2019/175277
PCT Pub. Date: Sep. 19, 2019

(65) Prior Publication Data
US 2021/0020025 A1    Jan. 21, 2021

(30) Foreign Application Priority Data
Mar. 14, 2018  (EP) .................................... 18305278

(51) Int. Cl.
| | | |
|---|---|---|
| *G08B 29/18* | (2006.01) | |
| *H04Q 9/00* | (2006.01) | |
| *G08B 21/04* | (2006.01) | |
| *A61B 5/0205* | (2006.01) | |
| *A61B 5/00* | (2006.01) | |

(Continued)

(52) U.S. Cl.
CPC ........ *G08B 29/188* (2013.01); *A61B 5/02055* (2013.01); *A61B 5/7275* (2013.01); *A61B 5/746* (2013.01); *G08B 21/0492* (2013.01);

*G08B 31/00* (2013.01); *H04Q 9/00* (2013.01); *A61B 5/021* (2013.01); *A61B 5/08* (2013.01); *A61B 5/1118* (2013.01); *A61B 5/14551* (2013.01); *A61B 5/318* (2021.01); *A61B 5/369* (2021.01);

(Continued)

(58) Field of Classification Search
CPC ................................................... G08B 29/188
See application file for complete search history.

(56) References Cited

U.S. PATENT DOCUMENTS

| 9,339,195 B2 | 5/2016 | Pitruzzello et al. |
| 2006/0015470 A1 | 1/2006 | Lauer et al. |

(Continued)

FOREIGN PATENT DOCUMENTS

WO    WO 2011/149565 A1    12/2011

OTHER PUBLICATIONS

International Search Report issued in International Application No. PCT/EP2019/056340, dated Jun. 6, 2019 (3 pages).

*Primary Examiner* — Travis R Hunnings
(74) *Attorney, Agent, or Firm* — Bookoff McAndrews, PLLC

(57) ABSTRACT

A system and a method for processing multiple signals generated by sensors processing to identify and/or monitor physiological data of an individual (for example in healthcare system) or general statement of an environment, a predetermined space (for example a room, a machine, a building) or an object (for example in smart home system, environment monitoring system, fire prevention system or the like).

18 Claims, 6 Drawing Sheets

(51) Int. Cl.
    *G08B 31/00*     (2006.01)
    *A61B 5/021*     (2006.01)
    *A61B 5/08*     (2006.01)
    *A61B 5/11*     (2006.01)
    *A61B 5/1455*     (2006.01)
    *A61B 5/318*     (2021.01)
    *A61B 5/369*     (2021.01)

(52) U.S. Cl.
    CPC ........... *A61B 5/4818* (2013.01); *A61B 5/6804* (2013.01); *A61B 5/7267* (2013.01)

(56) References Cited

U.S. PATENT DOCUMENTS

2016/0174903 A1   6/2016   Cutaia
2016/0271393 A1*  9/2016   Yu ..................... A61N 1/36842
2020/0191609 A1*  6/2020   Schmidt ................ G01F 9/001

* cited by examiner

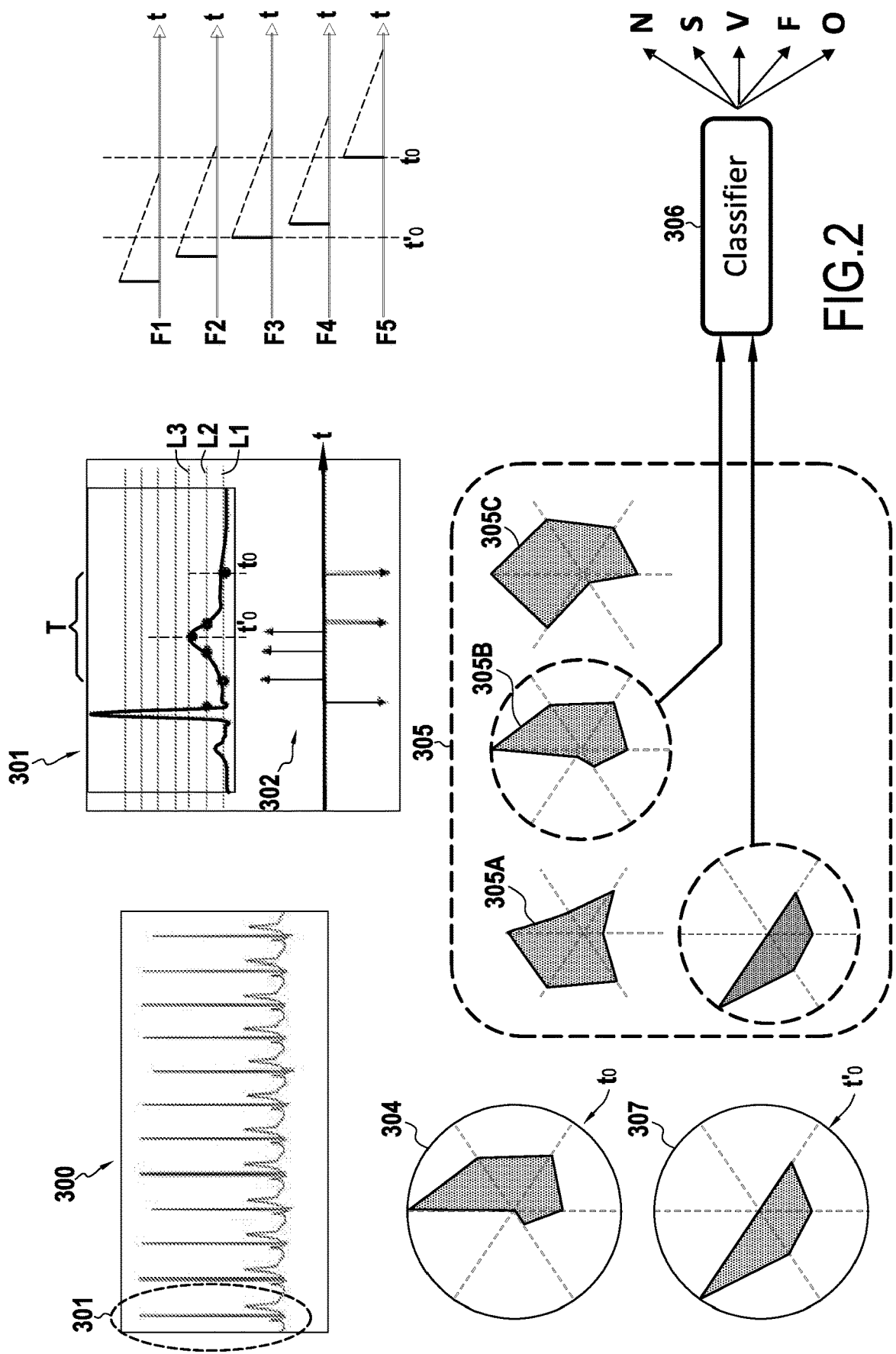

SYSTEM AND METHOD FOR PROCESSING MULTIPLE SIGNALS

CROSS-REFERENCE TO RELATED APPLICATION(S)

This application is the U.S. national phase entry under 35 U.S.C. § 371 of International Application No. PCT/EP2019/056340, filed on Mar. 13, 2019, which claims priority to European Patent Application No. 18305278.6, filed on Mar. 14, 2018.

FIELD OF THE INVENTION

The present Invention relates to the field of signals processing to identify and/or monitor physiological data of an individual (for example in healthcare system) or general statement of an environment, a predetermined space (for example a room, a machine, a building) or an object (for example in smart home system, environment monitoring system, fire prevention system or the like).

DESCRIPTION OF THE RELATED ART

It is now possible to acquire on, or in the vicinity of, an individual or object, a plurality of signals using multiple and/or various sensors. For example, it is possible with these sensors to obtain signal representative of electrocardiogram (ECG), electroencephalogram (EEG), respiration, blood pressure, presence of metabolite, temperature, individual physical activity or the like. Similarly, some of these sensors allow to obtain signal representative of room temperature, hygrometry, pH, heavy metal detection, humidity, air pressure, air quality, ambient light or the like.

According to one example, monitoring the signals delivered by these sensors allows determining individual specific physiological condition that might be impaired. For example, when an individual is having a seizure, specific signal features appear on the signals corresponding to the electrocardiogram (ECG) or to respiration.

According to another example, monitoring the signals delivered by smoke detector and temperature sensor from a predetermined space (e.g., a room) allows preventing fire occurrence.

U.S. Pat. No. 9,339,195 discloses a method in which seizure symptoms are detected. In this method, a sensor module receives plurality of isolated signals from plurality of sensors and a feature detection module detects plurality of isolated predefined features in said plurality isolated signals that are associated with seizure symptoms. The solution of this document is restricted to the detection of seizure symptoms, it requires a large amount of computational power and it is limited to the processing of isolated and independent signals. This existing technique does not correlate the various isolated signals and is therefore associated with a higher false positive rate in the detection of the seizure state.

Thus, there is a need for methods which are able to process multiple independent signals, wherein each of which can be of different scale, unit or system of measurement, by combining them in such a way that it becomes possible to detect occurrence and/or co-occurrence of any modification in the incoming signals. Hence the obtained combined processed data will provide more precise high-level information allowing to predict, identify or monitor individual or environment evolution and to alert in real-time in case of degradation.

SUMMARY OF THE INVENTION

The present Invention concerns a method for processing at least two signals produced by sensors, preferably by at least two sensors, the method comprising:
(i) receiving from sensors at least two signals, wherein at least one of said at least two signals is a temporal signal,
(ii) if the received temporal signal is not an asynchronous signal, the received temporal signal is converted into an asynchronous temporal signal comprising the events for said temporal signal, the said events being representative of each change of the said temporal signal,
(iii) analyzing each of said asynchronous signals received from one sensor, received in (i) and/or converted in (ii), and providing an activity profile of the said analyzed asynchronous signal, the activity profile comprising at least an activity value that varies as a function of the time (t) that has passed since the most recent event among the successive events of the said asynchronous signal,
(iv) at a given time t:
  a. determining a temporal context (t TC), said temporal context being defined as a set of activity profiles at said given time t of each of the said asynchronous signals,
  b. identifying a meta-event (t ME) by associating the said temporal context determined in step (a) with at least one temporal reference context selected from among at least two predefined reference temporal contexts,
  c. determining a meta-context (t MC) by determining the degree of correlation among the different meta-events identified in step (b),
  d. identifying a reference meta-context (t refMC) by association said meta-context determined in step (c) with at least one reference meta-context selected from at least two predefined reference meta-contexts.

According to preferred embodiment, step (iii) consists in analyzing each of said asynchronous signals received from one sensor, received in (i) and/or converted in (ii), and providing an activity profile of the said analyzed asynchronous signal or sensor, the activity profile comprising at least an activity value that decreases as a function of the time (t) that has passed since the most recent event among the successive events of the said asynchronous signal.

According to special embodiment, the said set of activity profile includes the activity profile of the closest events in time and/or space.

According to special embodiment, all the received signals from sensors are temporal signals.

According to special embodiment, all the received temporal signals are asynchronous signals.

According to special embodiment, all the received temporal signals are asynchronous signals and step (ii) is absent.

The following terms or definitions are only provided to assist in understanding the present invention. These definitions should not be interpreted as having ordinary skill in the range of less than understands the art.

"Event" designates occurrence triggered by a stimulus exceeding transition state.

"Event signal" designates any asynchronous signal consisting solely of a sequence of events "Asynchronous signal" consists in temporal signal characterized by a sequence of asynchronous events (called "event signal"). More particularly it designates any temporal signal whose values are adjusted or updated non-periodically i.e the time between two value adjustments may vary.

All these terms are well known in the art.

"Asynchronous signal", "event signal", "transformed temporal signal into a sequence of asynchronous events" are all "event based signals".

Step (ii) is optional and concerns embodiment of the method where the received temporal signal is not an asynchronous signal. Step (ii) consists in transforming the received temporal signal into a sequence of asynchronous events (called "event signal") that represents changes in the signal capture by the sensor at the time they occur. The following steps of the method comprises the analysis of said event signal using activity profiles as events are received with the asynchronous signal obtained from temporal signal.

The activity profile comprises, for each sensor or for each asynchronous signal (said asynchronous signals being received directly from sensor in (i) and/or being converted in (ii)), at least an activity value that varies as a function of the time that has passed since the most recent event among the successive events from said sensor. According to preferred embodiment, the activity profile comprises, for each sensor or for each asynchronous signal, at least an activity value that decreases as a function of the time that has passed since the most recent event among the successive events from said sensor Therefore the "activity profile" of a sensor or of an asynchronous signal can be seen as a curve as a function of time of which the value represents, at least, the time of the last event received for this sensor or for this asynchronous signal. It has been observed that the morphology of the activity profiles denotes the presence of certain basic patterns in the signal acquired by the sensor.

The "event signal" can be the set of events coming from a given sensor or a subset of these events (space subset: limited to certain time subset, limited to a given period of time).

According to special embodiment, the activity value of the activity profile varies exponentially as a function of the time that has passed since the most recent event among the successive events generated from one sensor.

According to preferred embodiment, the activity value of the activity profile decreases exponentially as a function of the time that has passed since the most recent event among the successive events generated from one sensor.

In a particular embodiment, the activity profile comprises, for each sensor or for each asynchronous signal, at least an activity value that varies, preferably decreases, as a function of the time that has passed since an event prior to the most recent event among the successive events from said sensor.

According to the present Invention, a reference meta-context determined in step (c) can be correlated to a specific physiological condition of an individual, for example a clinical state or medical condition. Alternatively, a reference meta-context can be correlated to a specific statement of an environment, a predetermined space or an object.

According to one special embodiment, the at least two signals are received in step (i) through a communication interface having a transmitter/receiver for transmitting and receiving said signals. According to special embodiment, said communication interface is working via a wired or wireless link.

The use of event based signals allows performing the association/correlation steps on more a limited set of information. This permits processing more signals generated by sensors.

According to preferred embodiment, the association in steps b or/and d is performed according to method of the art. According to one special embodiment, said association is made by calculating the distance between the considered context (temporal or/and meta-context) and corresponding reference context (i.e. reference temporal context or/and reference meta-context) belonging to a group of predetermined reference contexts, wherein said distance is a minimum distance.

According to another embodiment, said association step is made by methods from the field of machine learning such as Spiking Neural Networks (SNN), Multilayer Perceptrons (MLP) or an Auto-encoder (AE). Spiking Neural Networks may be preferably used for continuous identifications as these networks output an identified reference context is a detection threshold has been reached.

According to one special embodiment, for a same signal, a plurality of detections is carried out. Each predetermined feature to be detected has its own event signal. This allows performing a classification within the temporal signal, and improves the precision of the identification of a reference context.

According to preferred embodiment, at least two of the said received signals are of different scale, unit or system of measurement and/or are originating from different sensor types.

According to preferred embodiment, said received signals are selected in the group consisting of signals representative of electrocardiogram (ECG), electroencephalogram (EEG), respiration, blood pressure, body temperature, individual physical activity or the like.

Alternatively, said received signals are selected in the group consisting of signals representative of room temperature, hygrometry, pH, heavy metal detection, humidity, air pressure, air quality, ambient light or the like.

According to preferred embodiment, the method of the Invention comprises at least two temporal signals, preferably at least three temporal signals, event more preferably at least five temporal signals.

According to special embodiment, reference context (i.e. reference temporal context or/and reference meta-context) is associated with an event signal, and, when a reference context is identified, the event signal associated with this reference context is adjusted at a value and varies, preferably decreases, subsequently over time. According to special embodiment, each reference context is associated with an event signal, and, when a reference context is identified, the event signal associated with this reference context is adjusted at a value and varies, preferably decreases, subsequently over time.

It should be noted that the event signals associated with a reference signal and the event signals associated with pre-determined signal features mentioned in the present application have similar properties. For example, the value at which an event signal associated with a reference context is adjusted, and the duration of the variation, preferably the decrease, of such an event signal, may both be adjusted by the skilled person according to what the reference context represents.

The use of event signals associated with reference context according to the present Invention allows tracking each detection of a reference context in a manner which facilitates further processing.

According to another special embodiment, the method of the Invention further comprises the following step:

(v) at a given time t+n:

a'. determination of a temporal context (t+n TC), said context being defined as a set of activity profiles at said given time t+n of the said asynchronous signals, b'. identifying a meta-event (t+n ME) by associating each of said temporal context determined in step (a') with at least one temporal reference context selected from among at least two predefined reference temporal contexts, c'. determining of a meta-context (t+n MC) by determining the degree of correlation among the different meta-events identified in step (b') and arising from the said at least two signals, d'. identifying a reference meta-context (t+n refMC) by association of said meta-context determined in step (c') with at least one reference meta-context selected from at least two predefined reference meta-contexts.

According to special embodiment, t=t+n (n=0).

According to another special embodiment, t is different from t+n.

According to special embodiment n is 1.

According to special embodiment, reference context (i.e. reference temporal context or/and reference meta-context) is associated with an event signal, and, when a reference context is identified, the event signal associated with this reference context is adjusted at a value and varies, preferably decreases, subsequently over time. According to special embodiment, each reference context is associated with an event signal, and, when a reference context is identified, the event signal associated with this reference context is adjusted at a value and varies, preferably decreases, subsequently over time.

According to an embodiment, each reference meta-context identified in step (d') is associated with an event signal, and, when a reference meta-context is identified in step (d'), the event signal associated with this reference meta-context is adjusted at a value and varies, preferably decreases, subsequently over time.

The method of the Invention may be recursive. Subsequent meta-context can be deduced from one or more event signals based on one or more subsequent reference meta-context.

It should be noted that a classification based on a meta-context may only be performed if the required classifications identifying reference contexts have been carried out. The skilled person will be able to determine when each classification should be performed.

According to an embodiment, the identification of a first reference meta-context or second reference meta-context is preceded by the identification of at least one supplementary context at a third given time, the method further comprising a classification step of the reference meta-context and of the third reference meta-context to identify a reference signature of a period comprising the third given time and the given time or the second given time.

This embodiment allows using different reference meta-context which have been identified, to identify a state which is only visible on this period comprising the third given time and the first given time or the second given time.

The skilled person will know which classification method should be used to identify the signature.

According to an embodiment, the reference signature is associated with an event signal and, when a reference signature is identified, the event signal associated with this reference signature is adjusted at a value and varies, preferably decreases, subsequently over time.

In other words, in a manner which is similar to reference contexts, signatures are associated with event signals. It is possible to use these event signals for a context which may be determined after a signature has been identified, for example for classification purposes.

According to an embodiment, a meta-context is determined as also comprising the value of an indicator or of received data.

This indicator may also be designated by the person skilled in the art as a flag, for example a binary value which may be set at zero or one to indicate something.

By way of example, the user may set this indicator at "1" (or "0") to indicate a specific condition which may not be observable by a sensor, and this indicator will be taken into account in the classification step because it is part of a (second) context.

Alternatively, received data may be used. This data may be any additional information which is not acquired using a sensor or defined by an indicator.

According to an embodiment, performing a classification to identify a reference meta-context or a second reference meta-context or a signature further comprises identifying a future reference meta-context or signature (if the classification provides signatures) at a future given time.

In other words, classification that identifies a meta contexte which contribute to the definition of a prediction on future state (see FIG. 3A).

According to an embodiment, the method comprises delivering a probability value associated with this future reference meta-context. For example, this probability value indicates the probability that this future reference meta-context or signature is reached.

According to an embodiment, the method further comprises performing a further action taking into account an identified reference meta-context and/or an identified reference signature.

By way of example, this action may be triggering an alarm, sending a message, or operating a closed loop device (such as a syringe pump).

According to an embodiment, the at least one temporal signal is acquired on an individual and relates to physiological data of the individual.

The invention further relates to a system for processing signals wherein said system comprises one or more sensors that are able to generate signals, wherein at least one of said signal is temporal signal, and a processing unit that implements the method of the Invention.

According to one special embodiment, the one or more sensors are arranged on an item configured to be worn by an individual.

In this embodiment, the one or more sensors acquire physiological data of the individual.

By way of example, this item may be clothing such as a shirt or a t-shirt.

By way of example, this item may be an electronic patch positioned on the body of the individual.

The method of the Invention may be implemented by a processor of the separate device. This separate device may be a smartphone, a smartwatch, a tablet, etc. Communication between the sensors and the separate device and may be wired (for example via USB: Universal Serial Bus) or wireless (for example via Bluetooth).

In one particular embodiment, the steps of the as defined above are determined by computer program instructions.

Consequently, the invention is also directed to a computer program for executing the steps of a method as described above when this program is executed by a computer.

The invention further relates to a computer program, implementing all or a portion of the method described hereinabove, installed on pre-existing equipment.

The invention further relates to a non-transitory computer-readable medium on which is stored a computer program comprising instructions for the implementation of the method of the Invention, when this program is executed by a processor.

This program can use any programming language (for example, an object-oriented language or other), and by in the form of an interpretable source code, object code or a code intermediate between source code and object code, such as a partially compiled form, an entirely compiled code, or any other desirable form.

The information medium can be any entity or device capable of storing the program. For example, the medium can include storage means such as a ROM, for example a CD ROM or a microelectronic circuit ROM, or magnetic storage means, for example a diskette (floppy disk) or a hard disk.

Alternatively, the information medium can be an integrated circuit in which the program is incorporated, the circuit being adapted to execute the method in question or to be used in its execution.

In this embodiment, the device comprises a computer, comprising a memory for storing instructions that allow for the implementation of the method, the data concerning the stream of events received, and temporary data for performing the various steps of the method such as described hereinabove.

The computer further comprises a circuit. This circuit can be, for example:

a processor able to interpret instructions in the form of a computer program, or an electronic card of which the steps of the method of the invention are described in the silicon, or a programmable electronic chip such as a FPGA chip (Field-Programmable Gate Array).

This computer comprises an input interface for receiving signals from sensors. Finally, the computer can comprise, in order to allow for easy interaction with a user, a screen and a keyboard. Of course, the keyboard is optional, in particular in the framework of a computer that has the form of a touch-sensitive tablet, for example.

BRIEF DESCRIPTION OF THE DRAWINGS

How the present disclosure may be put into effect will now be described by way of example with reference to the appended drawings, in which:

FIG. 2 illustrates the processing of a single temporal signal is a schematic representation of the steps of a method in which second contexts are determined.

DESCRIPTION OF THE EMBODIMENTS

Figure 1:
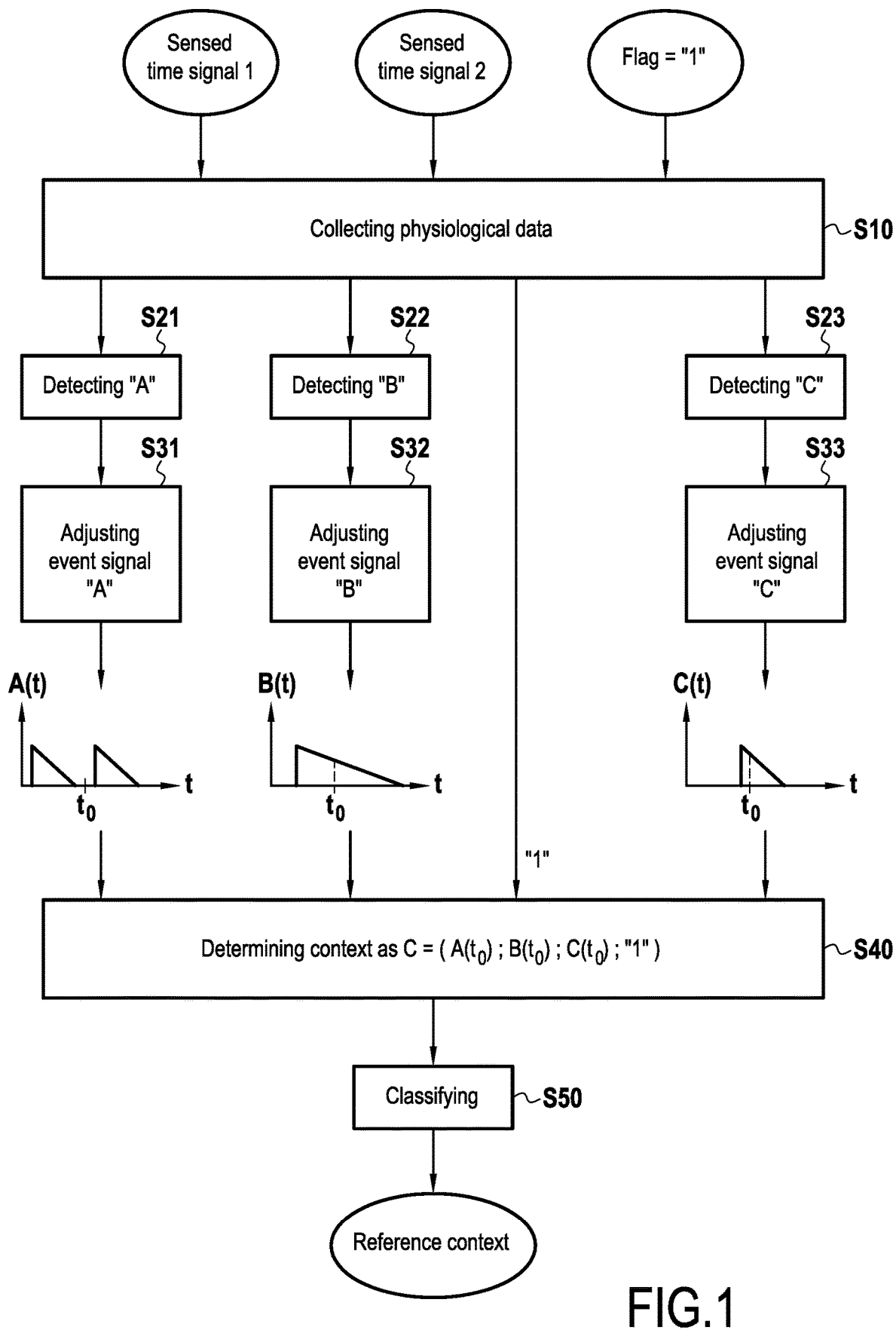
FIG. 1 is a schematic representation of the steps of the method for processing physiological data according to an example.

FIG. 1 illustrates the steps of the method for processing physiological data of an individual.

The invention is however not limited to processing physiological data of an individual and may also apply to signals which relate to an object or a room or a building.

In a first step S10, a step of collecting physiological data is carried out. This step may be carried out by receiving physiological data through a communication interface (for example through a wired or wireless interface). In other words, the method can be performed remotely with respect to the individual.

In the present example, the physiological data includes a first temporal signal, a second temporal signal, and an indicator or flag having the value "1".

The temporal signals may have been acquired on the individual and may be electrical signals of the analog type (i.e. continuous signals) or digital signals (i.e. sampled signals). By way of example, the first sensed signal may be an ECG signal, and the second sensed signal may be the output of a sensor which monitors the respiration of the individual.

It should be noted that in the present application, temporal signals are signals which have a value which vary over time.

The indicator having the value "1" may be, for example, an indicator which indicates a specific condition of the individual. For example, the indicator may indicate that the individual has undergone a specific surgery, or that the individual has taken drugs. Also for example, such an indicator may be acquired through a command of the user received in step S10.

It should be noted that step S10 may be carried out in a continuous manner, or quasi-continuous manner in which when new samples have been acquired for the temporal signals, these new samples are collected.

Detection steps S21, S22, and S23 are carried out once the temporal signals and the indicator have been collected or continuously along the collection of the temporal signals.

In step S21, a predetermined signal feature designated by "A" is detected in the first temporal signal. Feature "A", may be, for example, the first temporal signal reaching a predetermined value.

Each detection of feature "A" is followed by an adjusting step (step S31) in which a time signal associated with the feature "A" called event signal A(t) is adjusted at a value (for example 1). As can be seen on the figure, feature "A" is detected twice in the portion of time which is shown. The event signal A(t) is adjusted twice at the same value and subsequently. A(t) decreases over time in a linear manner with a predefined slope. This slope is chosen to illustrate the duration during which feature "A" remains relevant.

In step S22, a predetermined signal feature designated by "B" is detected in the first temporal signal. Feature "B", may be, for example, the width of a peak in the first temporal signal.

Each detection of feature "B" is followed by an adjusting step (step S32) in which a time signal associated with the feature "B" called event signal B(t) is adjusted at a value (for example 1). As can be seen on the figure, feature "B" is detected once in the portion of time which is shown. After having been adjusted at a value (for example 1), B(t) decreases over time in a linear manner with a predefined slope. As can be seen on the figure, this slope is not as steep as the slope shown for event signal A(t). Thus, feature "B" may have an impact on the individual which remains relevant for a longer time.

In step S23, a predetermined signal feature designated by "C" is detected in the second temporal signal. Feature "C", may be, for example, the second temporal signal reaching a predetermined value.

Each detection of feature "C" is followed by an adjusting step (step S33) in which a time signal associated with the feature "C" called event signal C(t) is adjusted at a value (for example 1). As can be seen on the figure, feature "C" is detected once in the portion of time which is shown. After having been adjusted at a value (for example 1), C(t) decreases over time in a linear manner with a predefined slope.

At a given time, in order to detect that the individual is in a particular state, it is possible to use the event signals and the flag. To this end, it is possible to use all the event signals which have been previously adjusted or a portion of the event signals.

Additionally, for a given detection, it is possible to adjust further an event signal, for example by applying a coefficient which is less than one to an event signal which is less significant for a specific detection. For example, there may be, for each type of detection, a hierarchy between the event signals which is embodied by coefficients applied to event signals. The skilled person will be able to determine these coefficients, for example during calibration steps.

Step S40 is carried out at a given time designated by t0. By way of example, step S40 may be performed at regular intervals, for example every minute. In this step, a context C is determined as comprising the value of each event signal at t0 and the flag at "1":

$$C=(A(t0);B(t0);C(t0);"1")$$

In this example, C is a vector comprising 4 components.

This context can then be used in a classification step S50 in which a reference context is identified. In this example, a group of reference contexts has been defined preliminarily, for example in a calibration step. Each reference context may be associated with a specific state of the individual.

Classification step S50 may be performed by means of a distance calculation (i.e. the distance between the context C and each reference context; the person skilled in the art will be able to determine which mathematical distance should be used), or also by means of methods from the field of machine learning such as Spiking Neural Networks (SNN), Multi-layer Perceptrons (MLP) or using Auto-Encoders (AE).

A reference context may then be identified.

FIG. 2 illustrates the processing, according to an example, of a single sensed signal 300, which is an ECG signal. This signal 300 comprises a plurality of QRS complexes well known to the person skilled in the art. The first QRS complex shown in the signal is designated by reference 301 it is also shown in more detail on the right of signal 300.

In the illustrated example, predetermined signal features relate to the temporal signal reaching predefined levels L1, L2, and L3 at specific instants of a duration T.

These predetermined features have been observed to allow the identification of various states of the individual. Every time these features are detected, a peak (other shapes of signal may be used) is generated on a signal 302. This signal 302 illustrates the detection of predefined features.

On signal 302, when a predefined level is reached by an increasing signal, a positive peak is generated. When a predefined level is reached by a decreasing signal, a negative peak is generated.

From the order of these peaks, it is possible to know which predefined feature has been detected.

Thus, it is possible to adjust corresponding event signals F1, F2, F3, F4, and F5 at a value every time the corresponding predetermined feature is detected. Each event signal F1 to F5 decreases right after the signal has been adjusted at a value.

At a given time t0, a context is determined as comprising all the value of event signals F1 to F5.

The context 304 is obtained. On the figure, this context 304 is represented in the form of a radar chart.

It is possible to identify a reference context using a classification method using the context 304 as input. For example, a distance between context 304 and a reference contexts may be used for the classification.

The identified reference context may belong to a group of reference contexts 305 comprising notably reference contexts 305A, 305B, 305C which have been represented on the figure (other reference contexts have not been represented for the sake of conciseness). Reference context 305B and the context 304 are graphically close and this reference context should be identified.

The identified reference context 305B, or a value corresponding to this reference context, is inputted to a classifier 306 which performs a further classification.

For example, at another given time t0', which may precede t0, it is possible to determine a context 307. It is possible to identify another reference context from the group of reference contexts. In this example, reference context 308 is identified.

Reference context 308, or a value corresponding to this reference context, is also inputted to the classifier 306.

For example, the classifier 306 may be able to detect 5 different signatures each designated by letters:
  N: Normal state;
  S: Supraventicular premature beat;
  V: Premature Ventricular contraction;
  F: Fibrillation; and
  O: Other, unclassified events.

These signatures may each be associated with an event signal. Also, the reference context N: Normal state may preferably not be associated with a second event signal in order to limit the quantity of data to be generated.

Preferably, reference context 306 uses a Spiking Neural Network, which may only output a signature if a predefined detection threshold has been reached.

Figure 3A:
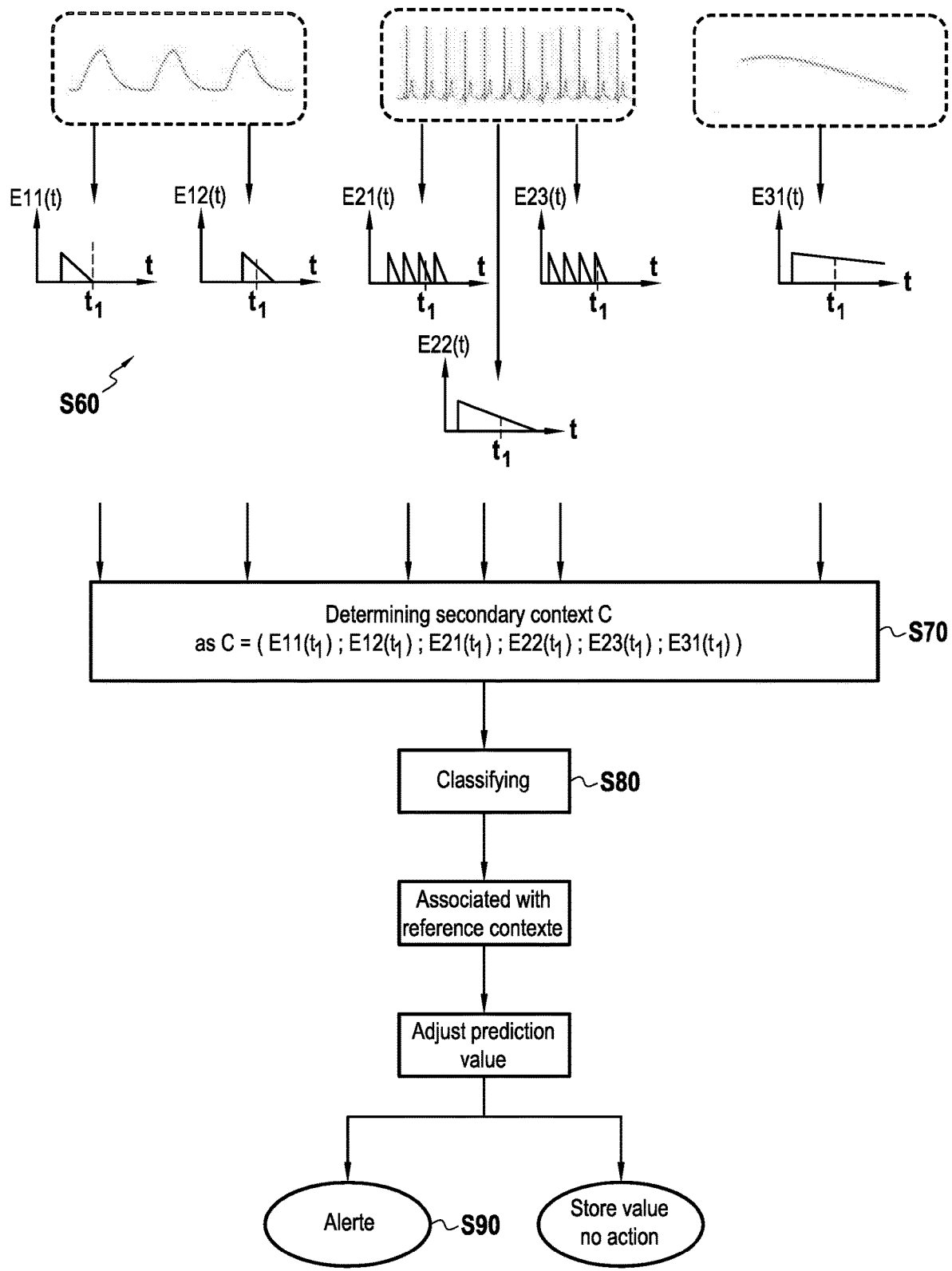
FIGS. 3A and 3B are a schematic representations of the steps of a method in which second contexts are determined.

FIG. 3A is an example of method in which second contexts are determined.

On this figure, different temporal signals are represented. These signals have been acquired on an individual. A first temporal signal 201 illustrates the respiration of the individual, a second temporal signal 202 illustrates the ECG of the individual, a third temporal signal 203 illustrates the temperature of the user. These temporal signals are all of different types.

For the temporal signal 201, by applying a method similar to the one disclosed in reference to FIG. 1 to only this temporal signal, two possible reference contexts may be identified. When one of these two reference contexts is identified, an event signal E11(t) corresponding to the reference context which has been identified is adjusted at a value (for example 1). Subsequently, the event signal E11(t) decreases over time in a manner which is analogous to the event signals described in reference to FIG. 1.

Similarly, when the other reference context is identified, an event signal E12(t) corresponding to this other reference context is adjusted at a value (for example 1). Subsequently, the event signal E12(t) decreases over time.

For the second temporal signal 202, three event signals corresponding to three different reference contexts are elaborated: E21(t), E22(t), and E23(t). It should be noted that alternatively one or more of these event signals may be associated with a signature which has been identified, as disclosed in reference to FIG. 2.

For the third temporal signal 203 one event signal corresponding is elaborated: E31(t). This event signal may be elaborated on the basis of the detection of a predetermined signal feature of signal 203.

From these event signals, it is possible to detect a state in which the individual is and which can be identified because this state has been observed to be associated with a plurality of specific contexts being identified within a timeframe: this implies that observing the corresponding event signals allows detecting this state.

For example, this detection may be performed regularly, for example every 24 h.

In order to be able to detect this state at a given time t1, a context C is determined as:

$$C=(E11(t1);E12(t1);E21(t1);E22(t1);E23(t1);E31(t1))$$

C is a vector of 6 components in this example.

This context C can then be used in a classification step S80 in which a second reference context is identified. In this example, a group of second reference contexts has been defined preliminarily, for example in a calibration step. Each second reference context may be associated with a specific state of the individual.

Classification step S80 may be performed by means of a distance calculation (i.e. the distance between the context C and each second reference context; the person skilled in the art will be able to determine which mathematical distance should be used), or also by means of methods from the field of machine learning such as Spiking Neural Networks (SNN) or Multilayer Perceptrons (MLP).

As shown on FIG. 2, the classification step outputs both a second reference context which has been identified, and a prediction.

This prediction comprises a second reference context which may be identified at t1+Δt, wherein Δt is a predefined duration. Additionally, the prediction may be associated with a probability value.

The skilled person will be able to select the appropriate classification method to be used to also output a probability value. This probability value may indicate the probability this second reference context to be identified.

It should be noted that event signals may be elaborated on the basis of an identification of a context or on the basis of an identification of a second context.

Figure 3B:
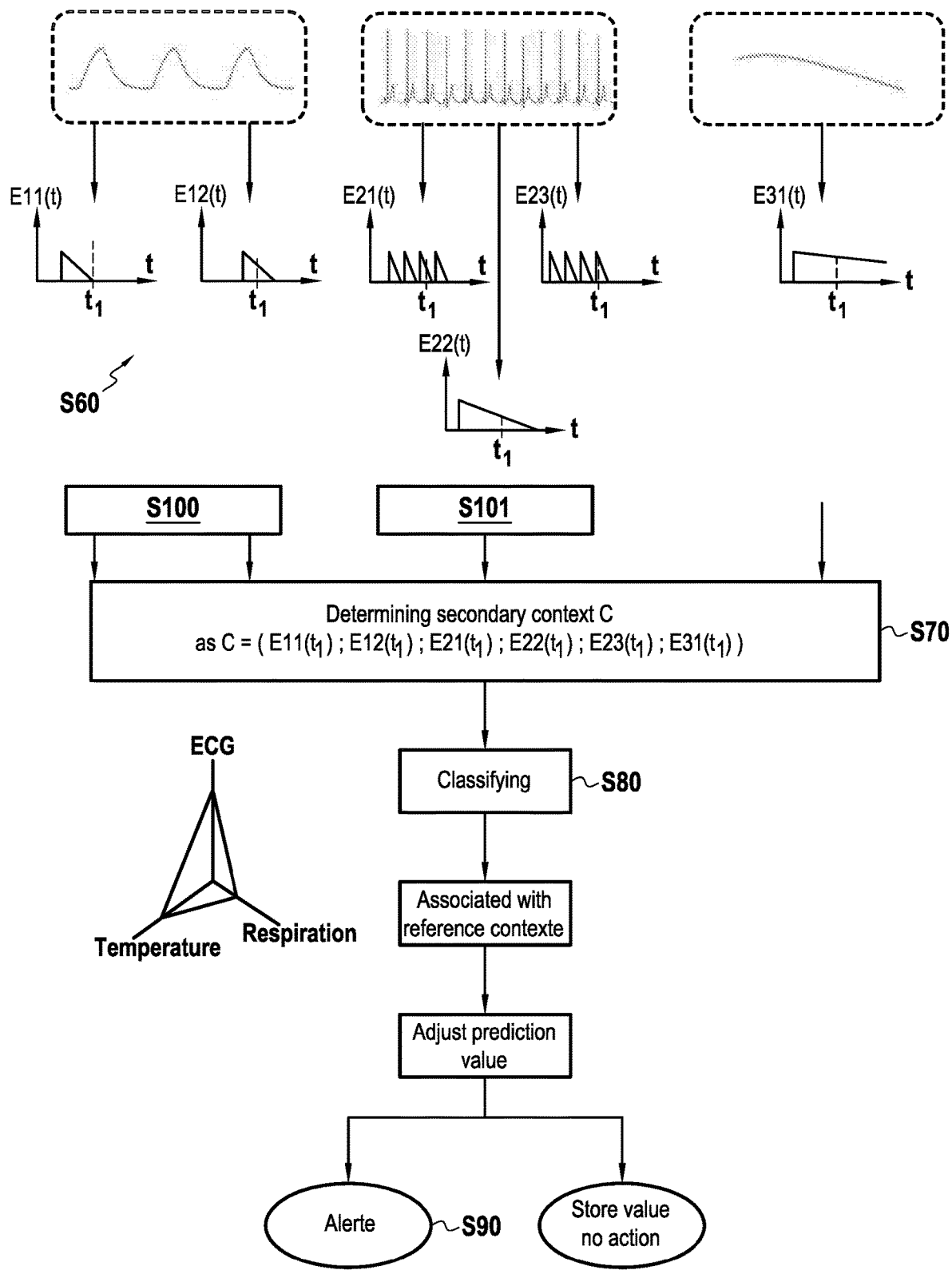

FIG. 3B is an alternative implementation of the method shown on FIG. 3A, in which the event signals E11(t) and E12(t) associated with temporal signal 201 are processed (step S100) to obtain a single value representing the state of these event signals at t1.

The event signals E21(t), E22(t) and E23(t) associated with temporal signal 202 are processed (Step S101) to obtain a single value representing the state of these event signals at t1.

Thus, this simplifies the determination of the context and the classification of step S80

As shown on the figure, a radar diagram showing the context has been represented. Each component is associated with a different physiological phenomenon.

Figure 4:
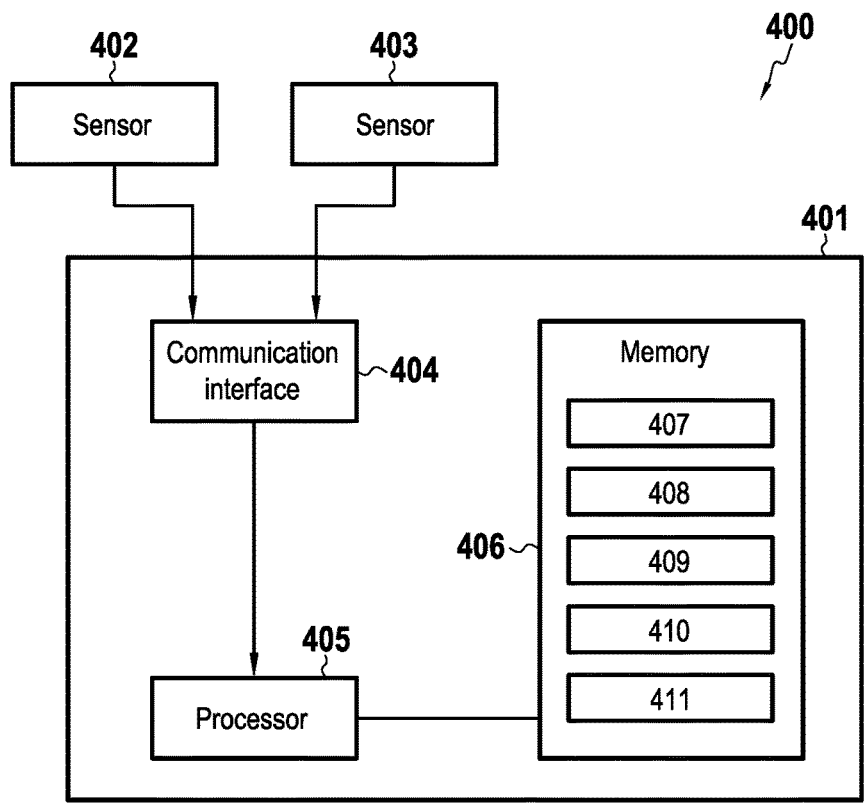
FIG. 4 is a schematic representation of a system according to an example.

FIG. 4 shows an example of system according to an example. This system may be configured to perform the various embodiments described in reference to FIGS. 1 to 3.

The system 400 comprises a device 401 which communicates with two external (with respect to the device 401) sensors 402 and 403. Communication may be obtained using a communication interface 404 of the device 401. For example, communication interface may be a wired communication interface such as a USB interface. Sensors 402 and 403 are configured to acquire temporal signals on an individual which constitute physiological data of the individual.

The device 401 further comprises a processor 405 which processes the temporal signals, and a non-volatile memory 406.

This non-volatile memory 406 comprises referenced contexts 407, and a set of instructions 408, 408, 410, and 411. When executed by the processor 405, these instructions and the processor 405 form modules of the device 401:

Instructions 408, when executed by processor 405, perform detecting, in the temporal signals acquired by sensor 402 and 403, at least one predetermined signal feature. Instructions 408 and the processor 405 form a detecting module that detects, in the temporal signals comprised signals, at least one predetermined signal feature.

Instructions 409, when executed by processor 405, perform adjusting at a value a time signal associated with the at least one predetermined signal feature called event signal, when the at least one predetermined signal feature is detected, the event signal subsequently decreasing over time. Instructions 409 and the processor 405 form an adjusting module that adjusts at a value a time signal associated with the at least one predetermined signal feature called event signal, when the at least one predetermined signal feature is detected, the event signal subsequently decreasing over time.

Instructions 410, when executed by processor 405, perform, at a given time, determining a context as comprising at least the value of the event signal at this given time. Instructions 410 and the processor 405 form a determining module that determines, at a given time, a context as comprising at least the value of the event signal at this given time.

Instructions 411, when executed by processor 405, perform a classification of the context so as to identify a reference context (from the reference contexts 407). Instructions 411 and the processor 405 form a classification module that classifies, at a given time, the context so as to identify a reference context.

Figure 5:
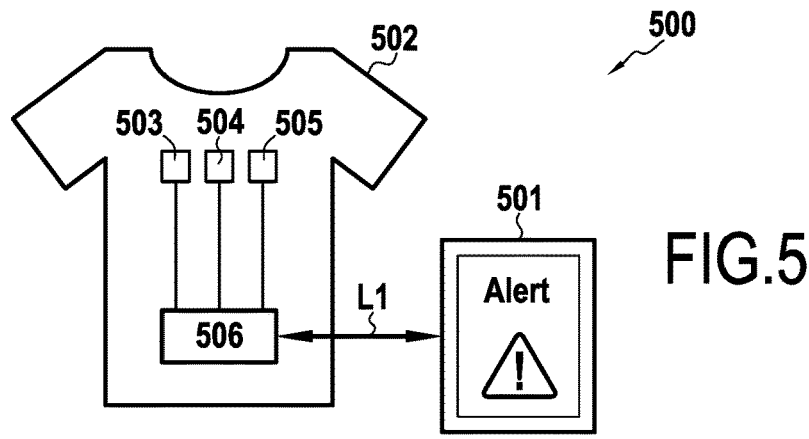
FIG. 5 is an schematic representation of a system comprising a clothing item.

On FIG. 5, a system 500 has been represented. This system comprises a device 501 which may be a smartphone and which is analogous to the device 401 described in reference to FIG. 4.

In this example, three sensors are shown as embedded in an item of clothing: a t-shirt. These sensors are referenced 503, 504, and 505. The three sensors 503 to 505 are connected to a communication module 506 which communicates wirelessly with the device 501 through communication link L1. The wireless communication may be performed using Bluetooth or any other appropriate wireless communication protocol.

As shown on the figure, the screen of the device 501 may display an alert message according to an identified reference context.

Figure 6:
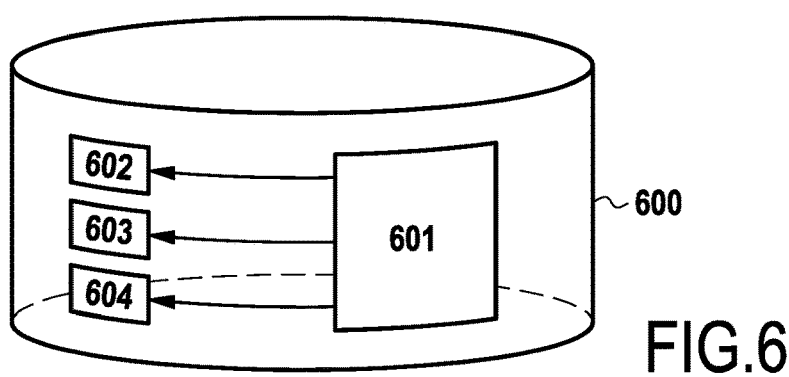
FIG. 6 is a schematic representation of a system comprising an alternative clothing item.

On FIG. 6, a system 600 has been represented. The system 600 may be in the form of an item of clothing: an armband.

This armband comprises a device 601 which is embedded in the armband and which is analogous to the device 401 described in reference to FIG. 4. The armband is also equipped with sensors 602, 604, and 604.

As can be understood from the above examples, the invention may be implemented in a compact manner.

The use of event signals also allows obtaining real-time results (for example contexts may be identified every second).

Also, the use of (second) event signals originating from different types of temporal signals allows identifying complex states of an individual. Thus, it is possible to improve the detection of states which may be detrimental, for example to an individual, so as to proactively protect the individual and/or to alert the individual.

Figure 7:
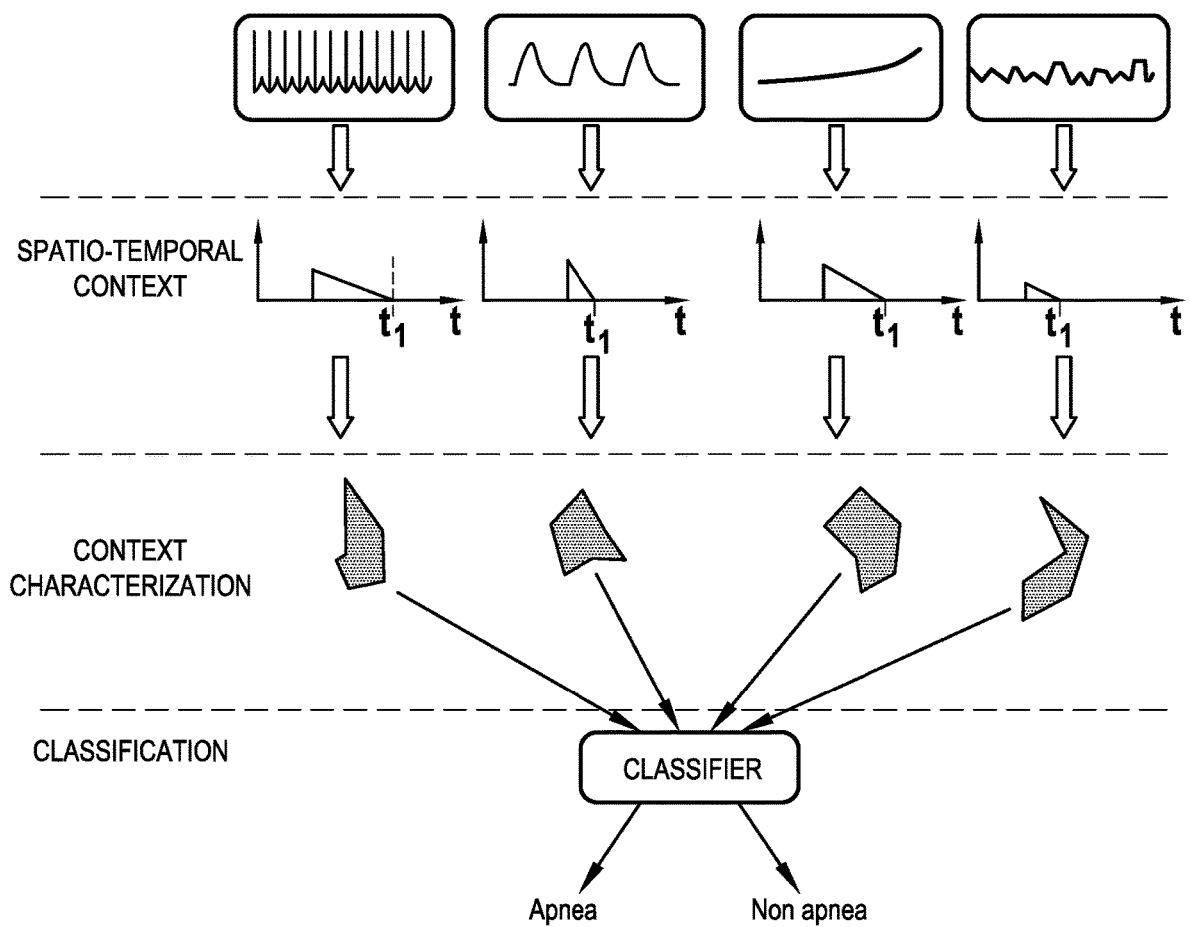
FIG. 7 is a schematic representation of sleep apnea detection using the fusion of ECG, respiratory signal, oximeter signal and EEG.

FIG. 7 illustrates the use of the data fusion method of invention to a multiparametric sleep apnea detector using the fusion of ECG, respiratory signal, oximeter signal and EEG.

Data fusion is the process of integrating multiple data sources to produce more consistent, accurate, and useful information than that provided by any individual data source. Features extraction is applied using method of the invention on each isolated signal from each sensor. The features are then combined to detect specific physiological condition (see FIG. 7).

Sleep apnea is often diagnosed using Polysomnography (PSG) method consisting in monitoring multiple physiological signals during overnight sleep. That is why the detection of this pathology is a good example to illustrate data fusion method of the invention. Sleep apnea is a sleep disorder characterized by pauses in breathing or periods of shallow breathing during sleep. Each pause can last from a few seconds to a few minutes and can happen many times a night. There are three forms of sleep apnea: obstructive (OSA), the most common form, central (CSA), and a combination of the two called mixed. The disorder disrupts normal sleep and it can lead to hypersomnolence, neurocognitive dysfunction, cardiovascular disease, metabolic dysfunction and respiratory failure. Sleep apnea is also a common pathology in epileptic patients, and can lead to death. Monitored signals usually include electroencephalography (EEG), airflow, thoracic or abdominal respiratory effort signals and blood oxygen saturation. The analysis of PSG requires dedicated personnel and is very time consuming. Moreover it involves inter-rater reliability variation in scorers. An automatic sleep apnea detection is therefore needed.

Performance Metrics:

Sleep apnea detectors are evaluated in terms of Se, SP, overall accuracy (ACC), and F1-score. These metrics relies on the number of true positives (TP: number of cases correctly identified as sleep apnea), true negatives (TN: number of cases correctly identified as non sleep apnea), false positives (FP: number of cases incorrectly identified as sleep apnea), and false negatives (FN: number of cases incorrectly identified as non sleep apnea) and are calculated as follow:

$$Se = \frac{TP}{TP+FN}, Sp = \frac{TN}{TN+FP}$$

$$F1\_score = \frac{2*Se*Sp}{Se+Sp}, ACC = \frac{TP+TN}{TP+FP+TN+FN}$$

Sensitivity (Se) refers to the ability to correctly detect sleep apnea, and specificity (Sp) evaluates the ability to correctly reject patients with no sleep apnea.

Results:

Data are 35 recordings of 7 hours to nearly 10 hours. Each recording includes an ECG signal, and only 4 recordings include also chest and abdominal respiratory eort signals. The presence or absence of apnea is indicated for each minute of each recording. Only OSA apneas are present in the dataset. Only recordings containing both ECG and respiratory signals are used, in order to evaluate the interest of data fusion. Apnea detection performance using a single parameter is compared with the detection using multiple parameters, by applying our method on respiratory signals only, and then on both signals (ECG+ respiratory signals). An increase of more than 15% in F1-score is obtained thanks to data fusion. However the size of the available dataset limits the learning and the results.

|  | Se | Sp | F1-score | Accuracy |
|---|---|---|---|---|
| Resp. only | 78% | 71% | 74% | 77% |
| Resp. + ECG | 89% | 90% | 89.5% | 89% |

The performance of the method was validated on another dataset: the MIT-BIH Polysomnographic Database, which is a collection of recordings of multiple physiologic signals during sleep. The database contains over 80 hours recordings of four, six, and seven-channel. Only 4 recordings include an ECG signal, an EEG signal, nasal, chest and abdominal respiratory eort signals, and an earlobe oximeter signal (SO2). Sleep stages and presence or absence of different types of apnea are indicated for each 30 s of each recording. The dataset contains different types of apnea, OSA and CSA, and different types of sleep stages (1, 2, 3, 4 and awake). The classification does not make any distinction between the different types of apnea, and portions of signal are classified into either "Apnea" or "Non-apnea". Signals are classified using only the respiratory effort signals. A F1-score of 81% is obtained. By combining the information of the ECG and the respiration a F1-score of 84% is obtained. The results are improved by first classifying portions of signals into different sleep stages. EEG is used to classify signals into 4 categories: "sleep stage 1", "sleep stage 2", "sleep stage 3 and 4", and "awake". Then ECG, respiratory, and oximeter signals are analyzed to classify recordings into "Apnea" or "Non-apnea". A F1-score of 94.4% is obtained. The results of classification keep increasing when we add more physiological signals.

|  | Se | Sp | F1-score |
|---|---|---|---|
| Resp. only | 74.5% | 91% | 81% |
| +ECG | 94% | 76% | 84% |
| +SO$_2$ + EEG | 91% | 98% | 94.4% |

CONCLUSION

Sleep apnea detection has been validated with two multiparametric database: the MIT-BIH Polysomnographic Database and the dataset from the CinC Challenge 2000. These databases contain multiple physiologic signals, and enable the evaluation of data fusion. Recordings consist of ECG, EEG, respiratory signals, and earlobe oximeter signal. By combining features from the ECG and from the respiratory signal, an increase of 15% in F1 score has been obtained, compared with features from respiration only, for the CinC Challenge 2000 dataset. The recordings from the MIT-BIH Polysomnographic Database present different types of apnea, and different sleep stages. Portions of signals were first classified into sleep stages, using the EEG information.

Then method of the invention was applied on the ECG, respiratory and oximeter signals. A sensitivity (Se) of 91% and a specificity (Sp) of 98% were obtained.

In conclusion, data fusion improves the results of apnea detection. Monitoring multiple physiological signals can lead to a better detection of different pathologies.

The invention claimed is:

1. A method for processing at least two signals produced by sensors, preferably by at least two sensors, the method comprising:
   (i) receiving from sensors at least two signals, wherein at least one of said at least two signals is a temporal signal,
   (ii) if the received temporal signal is not an asynchronous signal, the received temporal signal is converted into an asynchronous temporal signal comprising the events for said temporal signal, the said events being representative of each change of the said temporal signal,
   (iii) analyzing each of said asynchronous signals received from one sensor, received in (i) and/or converted in (ii), and providing an activity profile of the said analyzed asynchronous signal, the activity profile comprising at least an activity value that varies as a function of a time (t) that has passed since a most recent event among successive events of the said asynchronous signal,
   (iv) at a given first time:
      a. determining of a first temporal context (tTC), said first temporal context being defined as a set of activity profiles at said given first time of the said asynchronous signals,
      b. identifying a first meta-event (t ME) by associating the said first temporal context determined in step (a) with at least one temporal reference context selected from among at least two predefined reference temporal contexts,
      c. determining a first meta-context (t refMC) by determining a degree of correlation among the different first meta-events identified in step (b) and arising from the said at least two signals,
      d. identify a first reference meta-context by association said meta-context determined in step (c) with at least one reference meta-context selected from at least two predefined reference meta-contexts.

2. The method of claim 1 wherein step (iii) consists in analyzing each of said asynchronous signals received from one sensor, received in (i) and/or converted in (ii), and providing an activity profile of the said analyzed asynchronous signal or sensor, the activity profile comprising at least an activity value that decreases as a function of the time (t) that has passed since the most recent event among the successive events of the said asynchronous signal.

3. The method of claim 1 wherein all the received signals from sensors are temporal signals.

4. The method of claim 1 wherein all the received temporal signals are asynchronous signals and step (ii) is absent.

5. The method of claim 1, wherein a reference meta-context determined in step (c) can be correlated to a specific physiological condition of an individual.

6. The method claim 1, wherein at least two of the said received signals are of different scale, unit or system of measurement and/or are originating from different sensor types.

7. The method of claim 1, wherein said received signals are selected in a group consisting of signals representative of electrocardiogram (ECG), electroencephalogram (EEG), respiration, blood pressure, body temperature, individual physical activity or the like.

8. The method of claim 1 further comprising at least two temporal signals.

9. The method of claim 1 wherein at least two of said at least two signals are temporal signals.

10. The method of claim 1, further comprising:
   (i) at a given time t+n:
      a'. determination of a temporal context (t+n TC), said context being defined as a set of activity profiles at said given time t+n of the said asynchronous signals,
      b'. identifying a meta-event (t+n ME) by associating each of said temporal context determined in step (a') with at least one temporal reference context selected from among at least two predefined reference temporal contexts,
      c'. determining of a meta-context (t+n MC) by determining the degree of correlation among the different meta-events identified in step (b') and arising from the said at least two signals,
      d'. identifying a reference meta-context (t+n refMC) by association of said meta-context determined in step (c') with at least one reference meta-context selected from at least two predefined reference meta-contexts.

11. The method of claim 10 wherein t=t+n (n=0).

12. The method of claim 10 wherein t is different from t+n.

13. The method of claim 1 wherein the said reference temporal context or/and reference meta-context is associated with an event signal, and, when a reference context is identified, the event signal associated with this reference context is adjusted at a value and varies, preferably decreases, subsequently over time.

14. The method of claim 1 wherein the said method is recursive.

15. The method of claim 1 wherein the prediction comprises a second reference context which may be identified at $t1+\Delta t$ with $\Delta t$ is a predefined duration).

16. The method of claim 15, wherein the prediction is associated with a probability value.

17. The method of claim 15, wherein the prediction is associated with an alert.

18. A method for processing at least two signals produced by sensors, preferably by at least two sensors, the method comprising:
   (i) receiving from sensors at least two signals, wherein at least one of said at least two signals is a temporal signal,
   (ii) converting the received temporal signal into an asynchronous temporal signal, based on determining that the received temporal signal is not an asynchronous signal, the converted asynchronous temporal signal comprising events for said temporal signal, the said events being representative of each change of the said temporal signal,
   (iii) analyzing each of said asynchronous signals received from one sensor, received in (i) and/or converted in (ii), and providing an activity profile of the said analyzed asynchronous signal, the activity profile comprising at least an activity value that varies as a function of a time (t) that has passed since a most recent event among successive events of the said asynchronous signal,
   (iv) at a given first time:

a. determining of a first temporal context (tTC), said first temporal context being defined as a set of activity profiles at said given first time of the said asynchronous signals,
b. identifying a first meta-event (t ME) by associating the said first temporal context determined in step (a) with at least one temporal reference context selected from among at least two predefined reference temporal contexts,
c. determining a first meta-context (t refMC) by determining a degree of correlation among the different first meta-events identified in step (b) and arising from the said at least two signals,
d. identify a first reference meta-context by association said meta-context determined in step (c) with at least one reference meta-context selected from at least two predefined reference meta-contexts.

* * * * *

UNITED STATES PATENT AND TRADEMARK OFFICE
CERTIFICATE OF CORRECTION

PATENT NO. : 11,030,885 B2  
APPLICATION NO. : 16/980283  
DATED : June 8, 2021  
INVENTOR(S) : Sihem Kime et al.

Page 1 of 1

It is certified that error appears in the above-identified patent and that said Letters Patent is hereby corrected as shown below:

In the Claims

Column 15, Line 18, in Claim 1, after "comprising" delete "the".
Column 15, Line 62, in Claim 6, delete "method" and insert --method of--.
Column 16, Line 4, in Claim 8, delete "Claim 1" and insert --Claim 1,--.
Column 16, Line 6, in Claim 9, delete "Claim 1" and insert --Claim 1,--.
Column 16, Line 30, in Claim 13, delete "Claim 1" and insert --Claim 1,--.
Column 16, Line 37, in Claim 14, delete "Claim 1" and insert --Claim 1,--.
Column 16, Line 39, in Claim 15, delete "Claim 1" and insert --Claim 1,--.
Column 16, Line 41, in Claim 15, delete "duration)." and insert --duration.--.

Signed and Sealed this  
Tenth Day of August, 2021

Drew Hirshfeld  
*Performing the Functions and Duties of the*  
*Under Secretary of Commerce for Intellectual Property and*  
*Director of the United States Patent and Trademark Office*